(12) United States Patent
Nakajima

(10) Patent No.: US 8,884,766 B2
(45) Date of Patent: Nov. 11, 2014

(54) ANALYSIS SYSTEM, ANALYSIS METHOD AND ANALYSIS PROGRAM

(75) Inventor: Shinya Nakajima, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 244 days.

(21) Appl. No.: 13/455,395

(22) Filed: Apr. 25, 2012

(65) Prior Publication Data

US 2012/0268276 A1 Oct. 25, 2012

(30) Foreign Application Priority Data

Apr. 25, 2011 (JP) ................................. 2011-097399

(51) Int. Cl.
G08B 21/22 (2006.01)
G01N 33/493 (2006.01)

(52) U.S. Cl.
CPC .................................. *G01N 33/493* (2013.01)
USPC .......................... 340/573.1; 435/187; 436/73

(58) Field of Classification Search
USPC .......... 422/64; 435/287.1, 15; 436/73; 705/3; 600/551; 530/350; 340/573.1
See application file for complete search history.

(56) References Cited

U.S. PATENT DOCUMENTS

| | | | |
|---|---|---|---|
| 5,815,260 A | 9/1998 | Dou et al. | |
| 6,306,660 B1 | 10/2001 | Messenger et al. | |
| 7,820,449 B2 | 10/2010 | Kosaka | |
| 2002/0016443 A1* | 2/2002 | Keay et al. | 530/350 |
| 2005/0102166 A1* | 5/2005 | Tohma | 705/3 |
| 2006/0073606 A1* | 4/2006 | Fukuda | 436/155 |
| 2010/0159606 A1* | 6/2010 | Nakaminami et al. | 436/73 |
| 2010/0247377 A1* | 9/2010 | Tsutsumida et al. | 422/64 |
| 2010/0248347 A1* | 9/2010 | Tanaka et al. | 435/287.1 |
| 2010/0312137 A1* | 12/2010 | Gilmour et al. | 600/551 |
| 2012/0040387 A1* | 2/2012 | Matsuoka | 435/15 |

FOREIGN PATENT DOCUMENTS

| | | |
|---|---|---|
| CN | 1705883 A | 12/2005 |
| CN | 101852716 A | 10/2010 |
| CN | 101939640 A | 1/2011 |
| EP | 0769691 A2 | 4/1997 |
| EP | 0909953 A2 | 4/1999 |
| JP | 4226118 A | 8/1992 |
| JP | 9-171015 A | 6/1997 |
| JP | 2010-236863 A | 10/2010 |

OTHER PUBLICATIONS

Camici, et al., "Urinary detection of podocyte injury", Biomedicine and Pharmacotherapy, vol. 61, No. 5, Jun. 1, 2007, pp. 245-249.

* cited by examiner

*Primary Examiner* — Steven Lim
*Assistant Examiner* — Kaleria Knox
(74) *Attorney, Agent, or Firm* — Fox Rothschild LLP

(57) ABSTRACT

An analysis system includes: a creatinine information acquiring section to input creatinine measurement data that indicate a measurement quantity of creatinine in a urine sample; a material ingredient information acquiring section to input material ingredient data that indicate a measured quantity of a material ingredient in the urine sample; and a correcting section to correct the measured quantity of the material ingredient indicated as the material ingredient data, by use of the measured quantity of creatinine indicated as the creatinine measurement data.

9 Claims, 7 Drawing Sheets

ANALYSIS SYSTEM, ANALYSIS METHOD AND ANALYSIS PROGRAM

CROSS-REFERENCE TO RELATED APPLICATION

The present application is based upon and claims the benefit of priority of the prior Japanese Patent Application No. 2011-97399 filed on Apr. 25, 2011, the entire contents of which is incorporated herein by reference.

BACKGROUND OF THE INVENTION

1. Field of the Invention

The present invention relates to a urine test. In particular, the present invention relates to correction of a measured quantity of urinary material ingredient during data-processing by use of measured quantities of creatinine in the urine and the urinary material ingredient.

2. Description of Related Art

Conventionally, for example, in a biochemical examination of urine performed by using a test strip, concentrations of some elements such as protein, albumin, cholesterol and creatinine in the urine can be obtained. Though the concentrations of the urinary elements fluctuate depending on the urine amount, the amount of excreted creatinine in terms of time is constant. Therefore, it has been proposed to use the measured creatinine concentration for reference in correcting the concentrations of the other urinary elements. Specifically, it has been proposed to use as a measurement result the ratio of albumin to creatinine and to perform creatinine correction so as to acquire estimate values of the amounts of excrement per day of micro total protein, micro albumin and micro cholesterol.

In the conventional technique as mentioned above, only the urinary element concentrations obtained by the same measurement means as that of the creatinine are corrected, but there has not been any concept of using creatinine for correcting any urinary elements measured by means or methods different from that for creatinine.

SUMMARY OF THE INVENTION

An analysis system in one embodiment of the present invention includes: a creatinine information acquiring section to input creatinine measurement data that indicate a measured quantity of creatinine in a urine sample; a material ingredient information acquiring section to input material ingredient data that indicate a measured quantity of a material ingredient in the urine sample; and a correcting section to correct the measured quantity of the material ingredient indicated as the material ingredient data, by use of the measured quantity of creatinine indicated as the creatinine measurement data.

DETAILED DESCRIPTION OF THE INVENTION

In one embodiment of the present invention, it is possible to acquire both the measured quantity of a material ingredient and the measured quantity of creatinine different from each other in the measurement means and the measurement method and to correct the measured quantity of the material ingredient by use of the measured quantity of creatinine. For example, the measured quantity of a material ingredient such as bacteria and cast in urine may fluctuate depending on the condition in urine collection while the amount of creatinine excretion in terms of time is substantially constant. Therefore, for example, correcting the measured quantity of the material ingredient by use of the measured quantity of creatinine makes it possible to correct a fluctuation in the measured quantity caused by the urine collection condition. Thereby, it is possible to compensate the fluctuation in the measured quantity caused by the difference in the urine collection condition in the obtained information on the material ingredient in the urine. As a result, more multifaceted information on the amount of the material ingredient in the urine can be obtained.

According to the embodiments of the present invention, more multifaceted information on the amount of the material ingredient in the urine can be obtained by use of data obtained by different measuring means or different measurement methods.

[Embodiment 1]

(Configuration of Analysis System)

Figure 1:
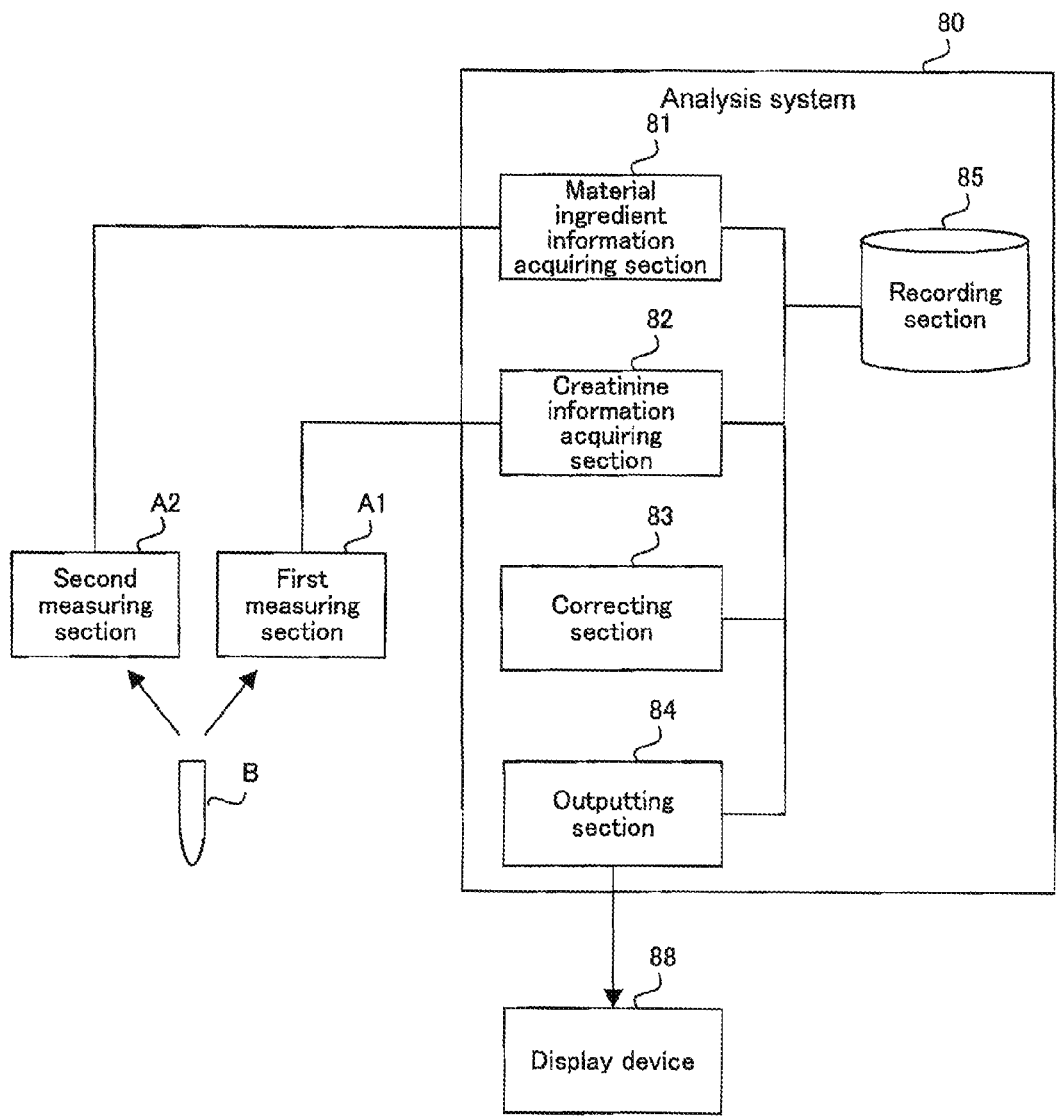
FIG. 1 is a functional block diagram showing a configuration example of an analysis system according to embodiment 1.

FIG. 1 is a functional block diagram showing a configuration example of an analysis system according to embodiment 1. In the example illustrated in FIG. 1, an analysis system 80 includes a material ingredient information acquiring section 81, a creatinine information acquiring section 82, a correcting section 83 and an outputting section 84. Furthermore, the analysis system 80 is connected to a first measuring section A1 and a second measuring section A2, and configured to be capable of receiving data or signals that indicate measurement results taken at these measuring sections. The first measuring section A1 and the second measuring section A2 are to measure the same urine sample B, but they are distinguished from each other in the measurement method and the elements to be measured. As mentioned above, the analysis system 80 acquires measurement results of respective elements in the urine sample measured by different measurement methods, and performs an analysis by using both of the measurement results.

The present embodiment mentioned below refers to an example where the first measuring section A1 is a measuring instrument to measure concentrations of creatinine and the like in the urine during a urinary qualitative test (urine chemistry test), and the second measuring section A2 is a measuring instrument to measure material ingredients such as bacteria and cast in the urine during a urinary sediment test. It should be noted that the combination of the first measuring section A1 and the second measuring section A2 is not limited to that in the present embodiment.

The first measuring section A1 can be configured, for example, to be capable of performing measurement of creatinine by use of a urine test strip. The first measuring section A1 may be used also to measure protein, albumin or the like as well as creatinine. In an specific example of such a case, the first measuring section A1 can include: a dispenser that divides the urine sample and feeds respectively to different reagents provided on a urine test strip; a photo-detector that detects transmitted light or reflected light that is generated as a result of irradiating with light the respective reagent into which the urine samples have been poured; and a computer that calculates elements in the urine sample with reference to the detected light.

The second measuring section A2 can be configured to be capable of measuring material ingredients in the urine by a liquid urine measurement for example. The second measuring section A2 may be used to measure for example leukocytes (white blood cells), erythrocytes (red blood cells), epitheliocytes (epithelium cells) and the like as well as bacteria and cast. In a specific example, the second measuring section A2 can include: a means for mixing in the urine sample a stain solution and a diluent and stirring; a means for irradiating with light the urine sample mixed with the stain solution and a diluent by flow cytometory so as to detect at least either transmitted light or scattered light; and a means for calculating elements in the urine sample with reference to the detected light.

The material ingredient information acquiring section 81 and the creatinine information acquiring section 82 function as interfaces to modify the information on the creatinine and the material ingredients measured at the first measuring section A1 and the second measuring section A2 to a state applicable at the analysis system 80. The material ingredient information acquiring section 81 inputs material ingredient data that indicate the measured quantity of the material ingredient in a urine sample. The creatinine information acquiring section 82 inputs creatinine measurement data that indicate the measured quantity of creatinine in the urine sample.

For example, the material ingredient information acquiring section 81 has a capability of receiving data or signals concerning a material ingredient in a urine sample B measured at the second measuring section A2 and recording the data or signals as material ingredient data that indicate measured quantity of the material ingredient in the urine sample, in a recording section 85 of the analysis system 80. Similarly, the creatinine information acquiring section 82 has a capability of receiving data or signals concerning creatinine in the urine sample B measured at the first measuring section A1 and recording the data or signals as creatinine measurement data indicating the measured quantity of creatinine in the urine sample B, in the recording section 85.

The measured quantity of creatinine indicated by the creatinine measurement data denotes the amount of creatinine contained in the urine sample obtained as a measurement result. The measured quantity may be for example a detected quantity such as absorbance and reflectance obtained directly through measurement. Alternatively, it may be an amount obtained on the basis of the detection signals, namely, an amount (e.g., concentration or the like) obtained indirectly by processing the detection signals. The format of the creatinine measurement data is not limited particularly. The creatinine measurement data may be for example a value to indicate the creatinine concentration in the urine or a value to indicate the detected quantity of light emitted by creatinine reacting with the reagent.

The measured quantity of the material ingredient indicated by the material ingredient measurement data denotes the amount of material ingredient in the urine sample obtained as the measurement result. Similarly to the above-described case of creatinine, this measured quantity may be for example a detected quantity such as absorbance or reflectance obtained directly by the measurement or it may be an amount obtained indirectly by processing the detection signals (e.g., absolute number per unit quantity). Similarly, the format of the material ingredient data is not limited in particular. For example, it may be a value to indicate the amount of bacteria (e.g., absolute number or concentration), a value to indicate the amount of cast, or a value to indicate the detected quantity of light from each of the stained bacteria and cast.

As the measured quantity of the material ingredients to be acquired as the material ingredient data, for example, a measured quantity of at least one of cast, erythrocytes, leukocytes, epitheliocytes, pathologic crystals, fungus, protozoan and parasites can be included. As each of the fungus, protozoan and parasites is an example of bacteria, each measured quantity may be acquired independently, or their measured quantities can be acquired together as a measured quantity of bacteria. Further, by acquiring as material ingredient data an element such as cast whose measured quantity fluctuates due to enrichment or an element such as bacteria whose measured quantity fluctuates due to propagation, the effect due to the correction as described below will be particularly remarkable. Though the present embodiment refers to an example for a case of acquiring measured quantities of bacteria and cast as measured quantities of material ingredients, material ingredients are not limited to these examples. Material ingredients include any kind of formed element which does not melt in the urine.

The correcting section 83 corrects the measured quantity of the material ingredient indicated as material ingredient data by using the measured quantity of creatinine indicated as creatinine measurement data. For example, the correcting section 83 can determine a corrected value of the measured quantity of the material ingredient on the basis of a value obtained by dividing the measured quantity of the material ingredient by the measured quantity of creatinine.

As a specific example, the correcting section 83 can set a corrected value as a value obtained by dividing concentrations of bacteria and cast by the creatinine concentration. Alternatively, the correcting section 83 may calculate the ratio of the concentrations of bacteria and cast to the creatinine concentration, or calculate by applying the ratio of bacteria and cast to creatinine as a corrected value.

Thereby, it is possible to obtain the information on the measured quantity of material ingredient normalized with the measured quantity of creatinine. As a result, for example, information to indicate the amounts of bacteria and cast can be obtained. And, fluctuations in the measured quantity caused by the urine collection conditions, such as a fluctuation in the measured quantity caused by a residence time, can be excluded from such information.

Measured quantities of some elements among many kinds of elements that are not measurable with a urine test strip tend to fluctuate depending on the conditions of enrichment or the urine collection. Examples of such elements include bacteria and cast. For example, the first urine excreted in the early morning and the urine excreted in the daytime are different from each other in the body residence time. The measured quantities of bacteria and the cast fluctuate due to the difference in the residence time. As a result of the above-mentioned correction by the correcting section 83, it is possible to obtain information from which the fluctuation in the measured quantity caused by the residence time has been excluded.

The outputting section 84 outputs the measured quantity (corrected value) that has been corrected by the correcting section 83 to a display device 88. The display device 88 may be a display provided to the analysis system 80 or an external display connected to the analysis system 80. The destination of the output from the outputting section 84 is not limited to the display device, but any outputting devices such as a printer and speaker can be the destinations for the output.

Here, it is possible that the correcting section 83 stores the corrected values of the measured quantity of the material ingredient for a plurality of measurements in the recording section 85 and that the outputting section 84 outputs the shift in the stored previous corrected values. Thereby, a user can check easily the transition of the corrected value. The correcting section 83 can record the corrected value in association with other necessary data such as material ingredient data, an identifier of a subject, information to indicate a measurement time (e.g. measurement date and time) and the like. Though the format of the recorded data is not limited in particular, for example, the corrected value and any associated data can be recorded in formats of a relational database and a measurement result file.

For example, as mentioned above, it is possible that the correcting section 83 conducts a correction of excluding a fluctuation caused by the residence time from the measured quantities of bacteria and cast, and stores the corrected values so as to display a history of corrected values of a same subject. In this case, it is possible to compensate influences from the residence time to the measurement results of bacteria and cast that have been collected under conditions with varied residence times. Thus, a history of the corrected amounts of bacteria and cast can be displayed. Therefore, the user can comprehend more precisely the transition in the amounts of bacteria and case.

(Operation Example of Analysis System 80)

Figure 2:
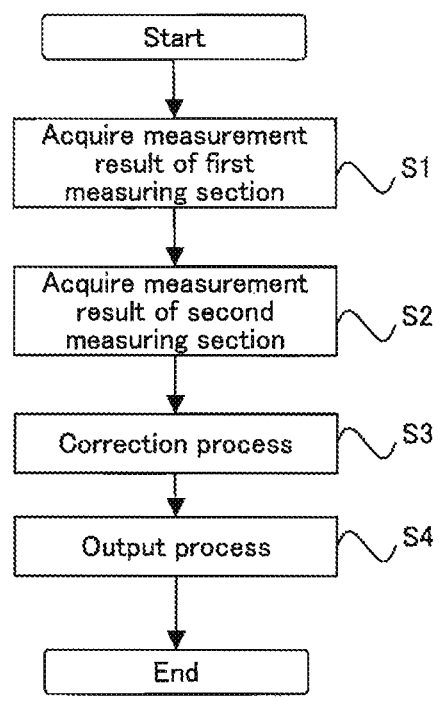
FIG. 2 is a flow chart showing an operation example of the analysis system.

FIG. 2 is a flow chart showing an operation example of analysis system 80. In the example as shown in FIG. 2, the creatinine information acquiring section 82 acquires first a measurement result of urine elements of the urine sample B measured by use of the test strip at the first measuring section A1 (step S1). This measurement result is regarded as including the creatinine concentration of the urine sample B for example. A measured value for creatinine concentration is recorded as the creatinine measurement data, in the recording section 85.

The material ingredient information acquiring section 81 acquires the measurement result of the material ingredient included in the sample B measured in the liquid urine measurement at the second measuring section A2 (step S2). This measurement result is regarded as including for example the number of bacteria and cast per unit amount of the urine sample B. The measured values of bacteria and cast are recorded as material ingredient data, in the recording section 85.

The correcting section 83 corrects the measured values of bacteria and cast acquired in the step S2 by use of the measured value of creatinine concentration acquired in the step S1 (step S3). For example, the correcting section 83 can calculate, as corrected values, the number of bacteria per unit amount/creatinine concentration and the number of cast per unit amount/creatinine concentration respectively. The corrected values are recorded in association with the material ingredient data before correction, in the recording section 85. In place of the creatinine concentration, reflectance of creatinine (in a case of using a test strip), absorbance of creatinine (in a case of measurement of transmission using a liquid reagent), a corrected value calculated from the creatinine concentration and the like can be used as the divisor for calculating the corrected value by division.

The outputting section 84 reads out the corrected value corrected by the correcting section 83 in the step S3 and allows the display device 88 to display the value. At this time, material ingredient data and/or creatinine measurement data may be displayed together with the corrected value. Further, the outputting section 84 may allow the display device 88 to display the history of the previous corrected values of bacteria and cast of the subject concerning the urine sample B that have been stored in the recording section 85.

Though the above-mentioned operation example refers to only creatinine, bacteria and cast, the analysis system 80 can display the measurement results of the other elements. For example, it is possible to display further the total protein, albumin, micro cholesterol, 'total protein/creatinine' and the like as the result of a urinary qualitative test by the first measuring section A1. Alternatively, it is possible to display further leukocytes, erythrocytes, epitheliocytes and the like as the result of an analysis on the urinary material ingredients by the second measuring section A2.

The operations of the analysis system 80 are not limited to the examples as shown in FIG. 2. For example, the processes in the step S1 and the step S2 may be performed concurrently or in a reversed order.

(Effects of the Embodiment and the Like)

According to the above-mentioned embodiment, measurement data that have been obtained at a measuring device (first measuring section A1) are used in a correction of measurement data obtained at another measuring device (second measuring section A2), and thus more multifaceted information can be obtained. Furthermore, since the fluctuation in the measured values caused by the urine collection condition can be corrected by use of creatinine, a more precise diagnosis will be available. In addition to that, by displaying the history of the corrected values, comparison with the previously measured value can be conducted easily, and thus estimation of advance of the state of a disease is conducted easily.

The functions of the functioning sections of the analysis system 80 as illustrated in FIG. 1, namely, the material ingredient information acquiring section 81, the creatinine information acquiring section 82, the correcting section 83 and the outputting section 84, can be realized by a computer provided with a processor that can execute a predetermined program recorded in a memory. The recording section 85 may be a recording medium provided to such a computer, or an external recording medium accessible from the computer. The recording medium may be a memory such as a flash memory to record temporarily data during a process at the processor, which is accessible at a high speed from the computer's processor. Alternatively, it may be a recording device such as HDD that can hold information even after the computer is turned off.

The analysis system 80 can be configured as an embedded computer included in a measuring device or a dedicated computer to be connected to a measuring device. Alternatively, it can be configured as a multi-purpose computer such as PC or a server provided independently from the measuring device. The analysis system 80 may be configured as a single computer or as a plurality of computers with distributed functions.

The present invention includes also embodiments of a program to allow a computer to function as an analysis system including the above-mentioned material ingredient information acquiring section 81, the creatinine information acquiring section 82 and the correcting section 83; and a recording medium (a non-transitory recording medium that does not include a transitional medium such as signals) on which such a program has been recorded.

The configuration of the analysis system 80 is not limited to the example as shown in FIG. 1. For example, the analysis system 80 may be a device configured integrally to include the first measuring section A1, the second measuring section A2 and the display device 88. Alternatively, the recording section 85 may be provided to the exterior of the analysis system 80.

In the above-mentioned embodiment, the material ingredient information acquiring section 81 and the creatinine information acquiring section 82 acquire measurement results from the first measuring section A1 and the second measuring section A2. However, acquisition of information is not limited to this example. For example, it may be an embodiment where data to indicate measurement results recorded in an external recording device are acquired via a network, which is made to be processible at the analysis system 80. Alternatively, it may be an embodiment where the analysis system 80 reads in a file or the like that indicates a measurement result recorded on an accessible recording medium so as to make it processible at the analysis system 80. The above alternatives can be applied also to the following embodiments 2 and 3.

[Embodiment 2]

Figure 3:
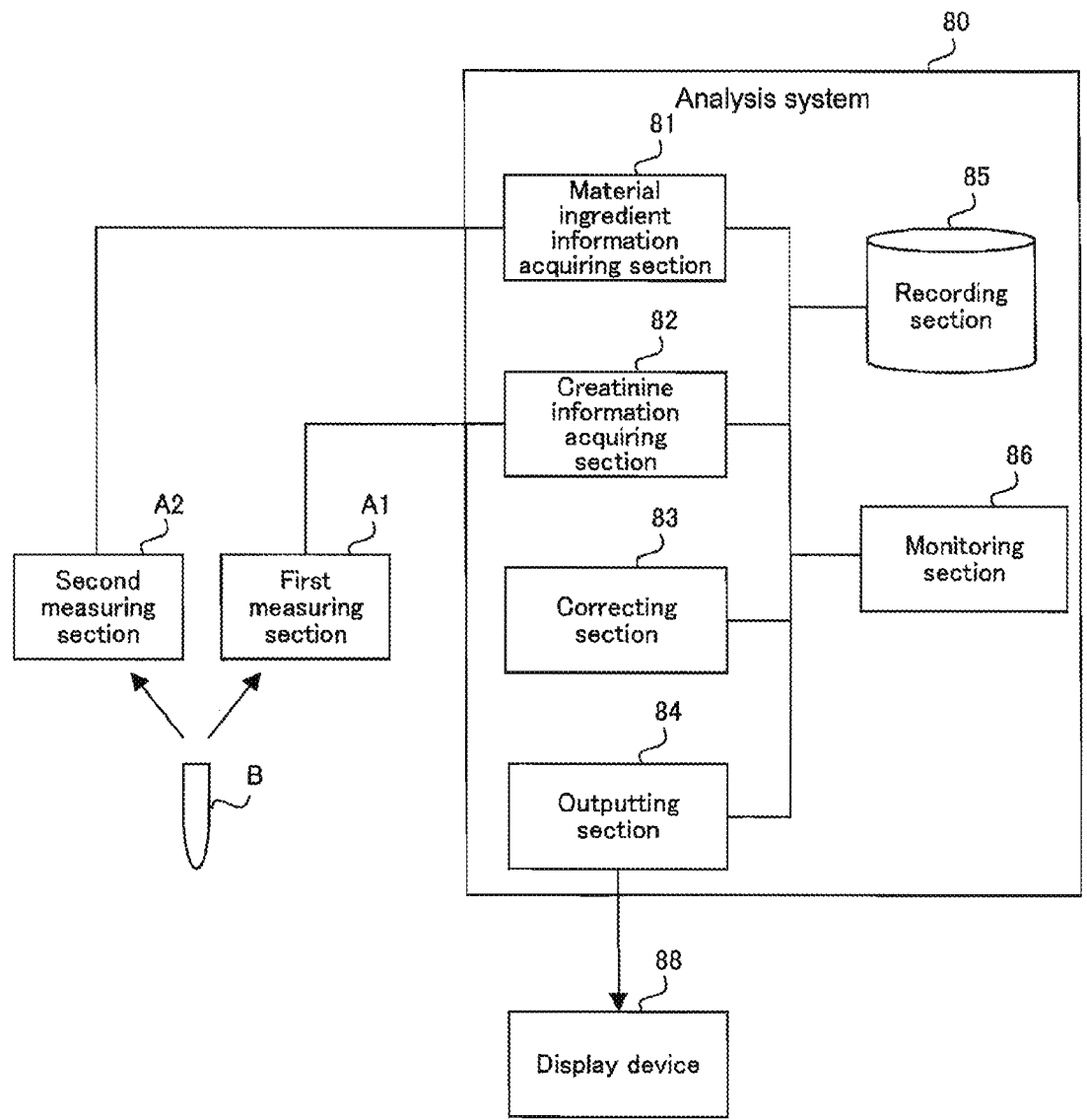
FIG. 3 is a functional block diagram showing a configuration example of an analysis system according to embodiment 2.

FIG. 3 is a functional block diagram showing a configuration example of an analysis system 80 according to embodiment 2. In FIG. 3, each functional block identical to that in FIG. 1 is assigned with the same reference number. The analysis system 80 in FIG. 3 is provided further with a monitoring section 86.

The monitoring section 86 monitors at least either the measurement data that has been recorded in the recording section 85 by the material ingredient information acquiring section 81 and by the creatinine information acquiring section 82 or a corrected value for the material ingredient that has been recorded in the recording section 85 by the correcting section 83, thereby deciding whether there is any abnormality or not.

For example, the monitoring section 86 has a capability of reading out a measured quantity before correction and a corrected value after correction for the material ingredient in the urine sample of the same subject that have been stored in the recording section 85 for the previous N-batches (N is a natural number) and making a decision of abnormality by use of the readout data. Specifically, the monitoring section 86 has a capability of making a comparison between the transition of the measured quantity before correction and the transition of the corrected value and making a decision of abnormality when the difference between the values indicating the transitions is out of the predetermined range. The transition can be represented by increasing/decreasing, or the variation. In this manner, by deciding whether the gap between the fluctuation in the measured quantity of a material ingredient before correction and the fluctuation in the corrected value after correction is within a tolerance or not, abnormality in the measurement environment and/or abnormality in the health status of the subject can be detected.

The monitoring section 86 may make a decision of abnormality on the basis of the measured quantity of the material ingredient obtained in a single measurement and the corrected value. For example, regarding each of the measured quantity before correction and the corrected value, the monitoring section 86 can decide whether each of the amount and the value is within a predetermined range, namely, whether they are respectively abnormal or not, thereby deciding abnormality based on both the decisions. For example, even if data to indicate a measured quantity before correction are below the threshold value of abnormality, the data can be decided as abnormal in a case where data after correction exceeds the threshold value of abnormality. In this case, abnormality in the measurement environment and/or abnormality in the health status of the subject can be detected.

Furthermore, the monitoring section 86 can make a decision on abnormality of creatinine measurement data. For example, abnormality of the creatinine value can be detected on the basis of the decision whether the fluctuation in the measured quantity of creatinine measured during a certain period is within a tolerance or not. This process of deciding abnormality in creatinine can be executed for example every time a measurement result for creatinine is obtained. Thereby, it is possible to check whether a creatinine measurement has been performed normally or not.

In a case where the monitoring section 86 makes a decision of abnormality, the outputting section 84 allows the display device 88 to display warning information.

(Operation Example 1)

Figure 4:
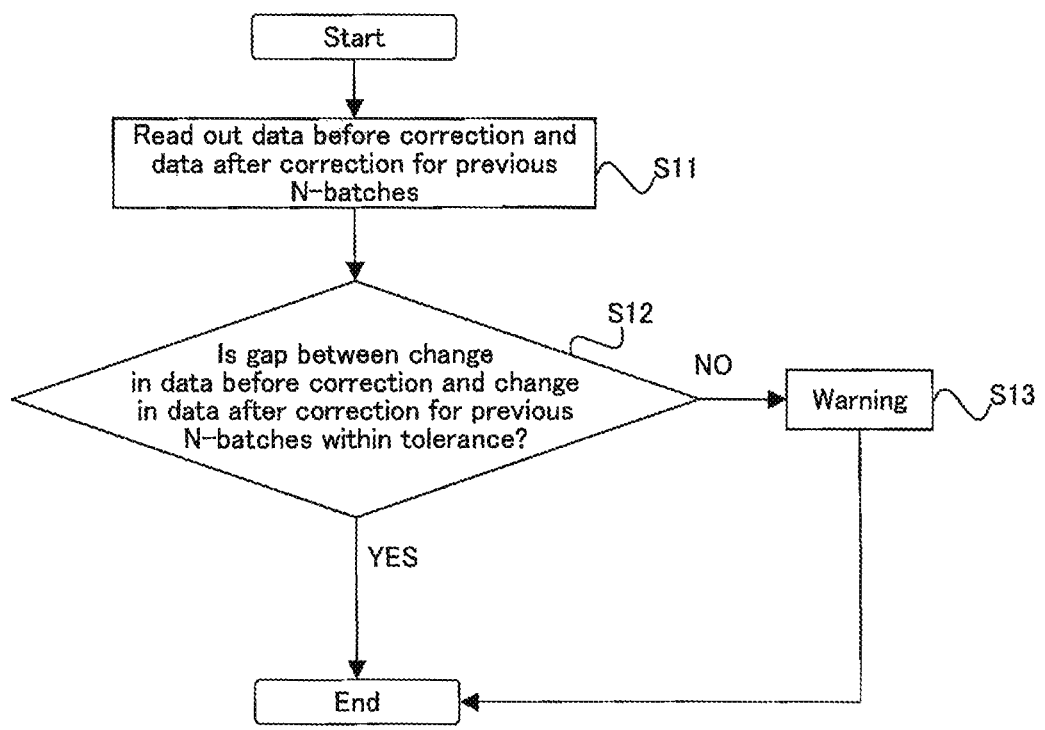
FIG. 4 is a flow chart showing an operation example of a monitoring section.

FIG. 4 is a flow chart showing an operation example of a monitoring section 86. In the example as shown in FIG. 4, first, the monitoring section 86 reads out, from the recording section 85, measured values before correction of a material ingredient for the previous N-batches and a corrected value after correction (step S11). For example, measured quantities and corrected values for bacteria and cast are read out.

The monitoring section 86 makes a comparison between the change in the measured values before correction and the change in the corrected values for the previous N-batches (step S12). For example, the monitoring section 86 counts, for each of the measured value before correction and the corrected value, the number of times that the value increases than a predetermined range and also the number of times that the value decreases than the predetermined range in comparison with the last value in the previous N-batches. If the counted number of the increases is greater than a threshold value, it can be decided that the value is on the increase. If the counted number of the decreases is greater than the threshold value, it can be decided that the value is on the decrease. When the corrected value after correction is increasing irrespective of the tendency of decrease of the measured value before correction, a determination of abnormality can be made, for example (NO in step S12). In this case, the outputting section 84 allows the display device 88 to display a warning regarding a necessity of a re-test together with a flag indicating that abnormality is found in the corrected value (step S22). Thereby, it is possible to urge the user to conduct a re-test and at the same time to inform that the cause of the abnormality is the corrected value.

The process illustrated in FIG. 4 may be executed by the monitoring section 86 periodically at a predetermined cycle or every time data for N-batches are stored. Alternatively, the monitoring section 86 may execute the process every time measurement data are added to the recording section 85 or execute on the basis of the user's instruction.

(Operation Example 2)

Figure 5:
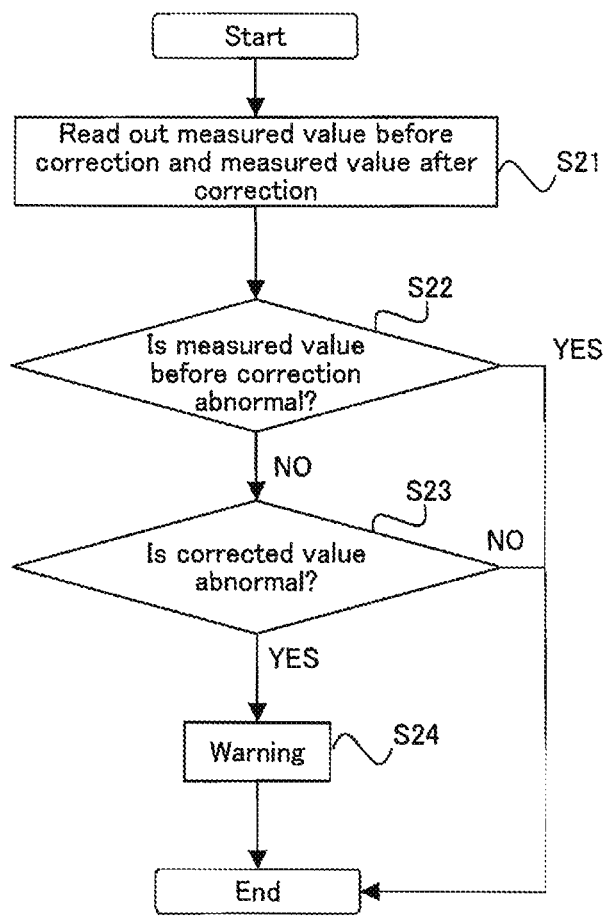
FIG. 5 is a flow chart showing another operation example of the monitoring section.

FIG. 5 is a flow chart showing another operation example of the monitoring section 86. In the example as shown in FIG. 5, the monitoring section 86 reads out data that indicate a measured quantity before correction as the material ingredient data measured this time and also the corrected value (step S21).

The monitoring section 86 decides whether the measured value before correction is abnormal or not, namely, whether the value is within a tolerance (step S22). The monitoring section 86 decides for example whether the number of bacteria and the number of cast exceed or not the range to be obtained in a normal measurement. In a case where the measured value before correction is not abnormal (NO in step S22), the monitoring section 86 decides whether the corrected value after correction is abnormal or not (step S23). In a case where the corrected value is abnormal (YES in step S23), then monitoring section 86 makes a decision of abnormality, and the outputting section 84 allows the display device 88 to display a warning regarding a necessity of retest together with a flag illustrating that the abnormality is found in the measured value (step S24).

The monitoring section 86 may execute the process as shown in FIG. 5 every time measurement data are added, or execute the process on the basis of the user's instruction. Further, the monitoring section 86 may be configured to execute both the processes as shown in FIGS. 4 and 5, or it may be configured to execute any one of the processes.

According to the present embodiment, since both the measured quantity before correction and the corrected value after correction are monitored, it is possible to detect an abnormality that will be overlooked according to a conventional technique. For example, while urinary creatinine is regarded as stable for several days at room temperature, bacteria in urine increases over time during a retention at room temperature. Therefore, by calculating a value of bacteria/creatinine (bacteria-creatinine ratio) and monitoring the change over time, it is possible to detect abnormality such as an error in the measured value (for example, unfavorable preservation condition or the like).

[Embodiment 3]

Embodiment 3 is an embodiment of a urine analyzer including an analysis system.

(General Configuration)

Figure 6:
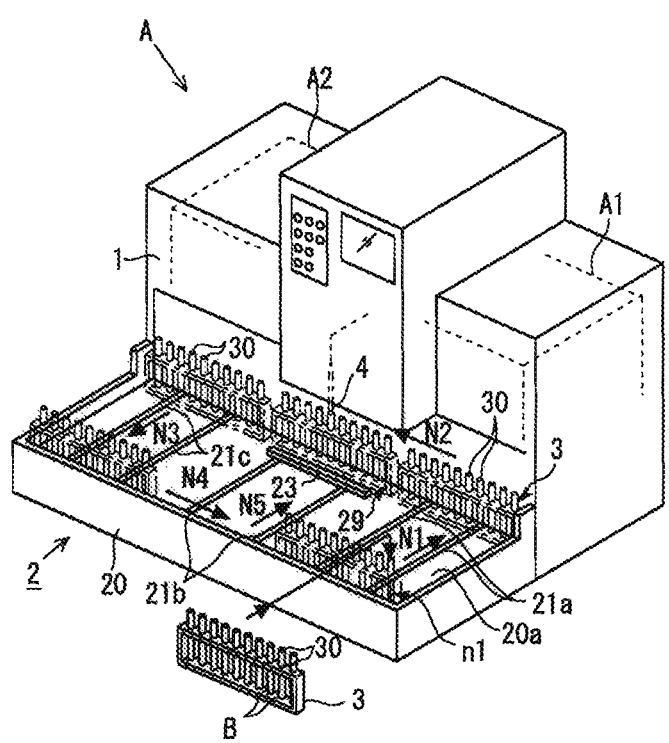
FIG. 6 is an external view of a urine analyzer in embodiment 3.
Figure 7:
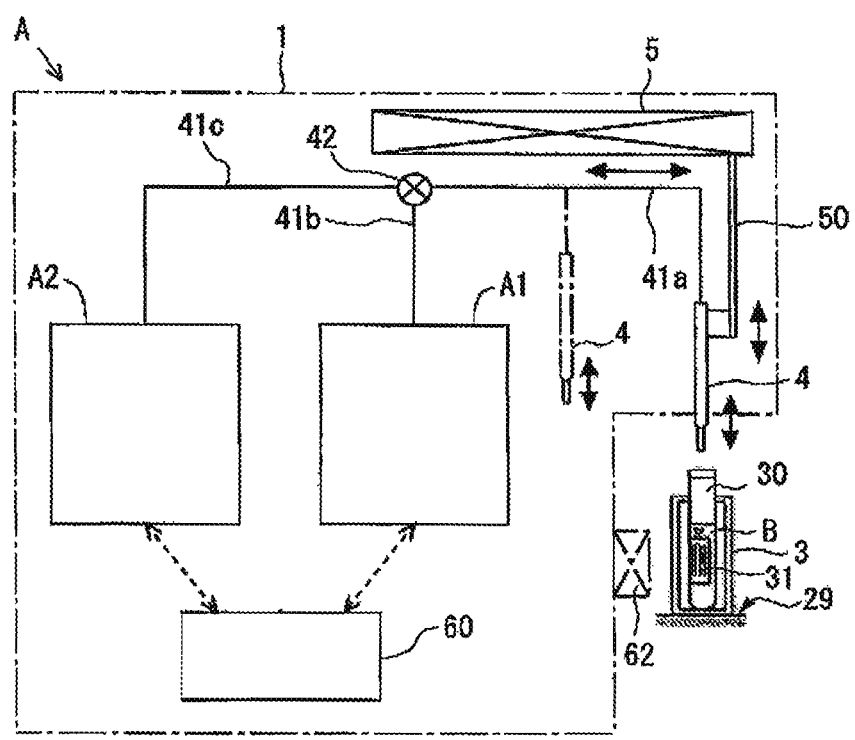
FIG. 7 is a diagram showing the internal configuration of the urine analyzer.

FIGS. 6 and 7 are diagrams showing a configuration example of a urine analyzer in the present embodiment. FIG. 6 is an external view of an analyzer and FIG. 7 is a diagram showing the internal configuration of the analyzer.

As shown in FIGS. 6 and 7, a urine analyzer A according to the present embodiment has a first measuring section A1 and a second measuring section A2 contained in a single housing 1. The first measuring section A1 and the second measuring section A2 perform analyses different from each other with regard to a specimen to be analyzed. Here, an analysis performed at the first measuring section A1 is called a first analysis while an analysis performed at the second measuring section is called a second analysis.

Specifically, the first analysis is a urinary qualitative test and the second analysis is a urinary sediment test. In the urinary qualitative test, concentrations of protein, glucose, hemoglobin and bilirubin or the like included in the urine, the specific gravity of urine and the like are measured. In the urinary sediment test, material ingredients such as hemocyte, epitheliocytes, bacteria, crystals and the like contained in the urine are measured. For the first measuring section A1, any specific configuration applicable to the urinary qualitative test can be employed. For the second measuring section A2, any specific configuration applicable to the urinary sediment test can be employed. The first analysis and the second analysis are different from each other in the analytical items and the analytical forms.

The urine analyzer A includes a conveyer 2. The conveyer 2 is a device to convey a plurality of glass tubes containing urine B as a specimen (corresponding to a urine sample). The conveyer 2 conveys the glass tubes 30 that are held standing in a specimen rack 3. The conveyer 2 has a frame 20 joined to the front-bottom of a housing 1, three pairs of belts 21a, 21b and 21c that are provided to the upper face part 20a of the frame 20 and that can be driven to circulate, and two pushers (not shown) that can travel in the horizontal direction.

In the conveyer 2, when the specimen rack 3 is supplied to the position indicated with the reference number n1, the specimen rack 3 is conveyed by the belt 21a in a direction indicated with an arrow N1, and then conveyed by one of the pushers in a direction indicated with an arrow N2. Subsequently, the specimen rack 3 is conveyed by the belt 21c in a direction indicated with an arrow N3, and then conveyed by the other pusher in a direction indicated with an arrow N4 so as to be supplied onto the belt 21b.

Furthermore, the urine analyzer A has a nozzle 4 to collect the urine B to be analyzed from the glass tubes 30 conveyed by the conveyer 2. The nozzle 4 is disposed at a position to overlap with a conveyer route 29 for the specimen rack 3 to be conveyed in the N2 direction. The nozzle 4 aspirates the urine B from the glass tubes 30 held in the specimen rack 3 on a conveyer route 29. Thereby, the nozzle 4 collects the urine B to be analyzed.

As shown in FIGS. 6 and 7, the urine analyzer A according to the present embodiment does not have any other nozzles than the nozzle 4 that collects the urine sample. Namely, both of the urine sample to be fed to the first measuring section A1 and the urine sample to be fed to the second measuring section A2 are collected through the nozzle 4. In this manner, by sharing a nozzle between the first measuring section A1 and the second measuring section A2, a part of the channels to feed the urine sample to the respective measuring sections A1 and A2 and a cleaning device to clean the nozzle can be shared similarly. As a result, the size of the urine analyzer A itself can be reduced and the cost for producing the urine analyzer A can be decreased.

Here, the internal configuration of the urine analyzer A according to the present embodiment will be described below with reference to FIG. 7. A nozzle carrier 5, urine channels 41a, 41b, 41c, a three-way valve 42, and a controlling section 60 as well as the first measuring section A1 and the second measuring section A2 are provided to the interior of the urine analyzer A.

The nozzle carrier 5 has an arm 50 to support the nozzle 4. The nozzle carrier 5 travels the nozzle 4 vertically and horizontally (a direction indicated with arrows in FIG. 7) via the arm 50.

One of the end parts of the common urine channel 41a is connected to the nozzle 4. The other end part of the common urine channel 41a is connected to the three-way valve 42. To the three-way valve 42, one end part of each of the first and second urine channels 41b and 41c is connected. The three-way valve 42 is capable of switching the channel for the urine B that has been collected through the nozzle 4, from the common urine channel 41a to the first urine channel 41b or to the second urine channel 41c.

And the other end part of the first urine channel 41b is connected to the first measuring section A1, and the other end part of the second urine channel 41c is connected to the second measuring section A2. Namely, the urine B collected through the nozzle 4 is fed to the first measuring section A1 through the common urine channel 41a and the first urine channel 41b, and also is fed to the second measuring section A2 through the common urine channel 41a and the second urine channel 41c.

The controlling section 60 is a computer provided with CPU, a memory and the like (not shown). The first measuring section A1, the second measuring section A2, the nozzle carrier 5, the three-way valve 42 and the like are connected electrically to the controlling section 60. The controlling section 60 performs processing of data on the analysis results at the respective analyzers A1, A2, and controls the operations of the respective sections (or devices) mentioned above. The controlling section 60 can have the functioning sections of the analysis system as shown in FIG. 1, namely, the material ingredient information acquiring section 81, the creatinine information acquiring section 82, the correcting section 83, the outputting section 84 and the recording section 85. In this manner, in the present embodiment, the entire urine analyzer A is controlled by the single controlling section 60.

As illustrated in FIG. 7, an identification code 31 such as a bar code is placed on the glass tube 30. The urine analyzer A includes a reading section 62 to read this identification code 31. The reading section 62 also is connected electrically to the controlling section 60, and thus identification data that have been read by the reading section 62 are inputted into the controlling section 60. And, the thus inputted identification data are utilized as reference data to be associated with the data of the analysis results on the urine B at the respective measuring sections A1 and A2.

Furthermore, though not shown in the attached drawings, a cleaning device for cleaning the interior of the nozzle 4 is provided inside the urine analyzer A. The cleaning device includes a cleaning liquid tank to reserve a cleaning liquid, a feeder to feed the cleaning liquid from the tank into the nozzle 4, and a liquid waste tank to contain liquid wastes discharged from the nozzle 4 after cleaning the nozzle 4. In the urine analyzer A, a specimen is collected by the nozzle 4, the specimen is fed to the respective measuring sections A1 and A2, and the nozzle 4 is cleaned by the cleaning device before collecting a next specimen to be analyzed.

As mentioned above, the first measuring section A1, the second measuring section A2 and the analysis system 80 can be integrated to configure the urine analyzer A. The urine analyzer A includes further a conveyer to convey urine samples to the first measuring section A1 and the second measuring section A2 respectively, and a nozzle and/or a channel (feeder) to feed the urine samples to the first measuring section A1 and the second measuring section A2 respectively.

The configuration of the urine analyzer A is not limited to the example as illustrated in FIGS. 6 and 7. For example, the urine analyzer can include further a short-time analyzing section that derives an analysis result in a shorter time in comparison with the first analysis by the first measuring section A1, and also a determining section that determines whether to execute or not the second analysis by the second measuring section A2 on the basis of the analysis result at the short-time analyzing section.

The present invention can be used or utilized, for example in the field of urine analyzing equipment and the like.

The invention may be embodied in other forms without departing from the spirit or essential characteristics thereof. The embodiments disclosed in this application are to be considered in all respects as illustrative and not limiting.

What is claimed is:

1. An analysis system comprising:
   a creatinine information acquiring section to input creatinine measurement data that indicate a measured quantity of creatinine in a urine sample;
   a material ingredient information acquiring section to input material ingredient data that indicate a measured quantity of a bacteria or cast in the urine sample; and
   a correcting section to correct the measured quantity of the bacteria or cast in the urine sample indicated as the material ingredient data, by use of the measured quantity of creatinine indicated as the creatinine measurement data.

2. The analysis system according to claim 1, wherein the correcting section determines a corrected value of the measured quantity of the bacteria or cast in the urine sample on the basis of a value obtained by dividing the measured quantity of the bacteria or cast in the urine sample by the measured quantity of the creatinine indicated as the creatinine measurement data.

3. The analysis system according to claim 1, wherein the correcting section stores a corrected value of the measured quantity of the bacteria or cast in the urine sample in a recording section, and the analysis system further comprises an outputting section to output a shift of the previous corrected values stored in the recording section.

4. The analysis system according to claim 3, wherein the correcting section stores in the recording section the corrected value and the material ingredient data before correction in association with each other,
   the analysis system further comprises a monitoring section to monitor so as to find abnormality in the fluctuations of the corrected value stored in the recording section and the material ingredient data before correction stored in the recording section, and
   in a case where the monitoring section finds abnormality, the outputting section outputs a warning.

5. The analysis system according to claim 1, further comprising a first measuring section to measure creatinine in the urine sample, and a second measuring section to measure a bacteria or cast in the urine sample.

6. The analysis system according to claim 3, wherein the monitoring section monitors further to find abnormality in the fluctuation of the creatinine measurement data, and
   in a case where the monitoring section finds abnormality in the fluctuation of the creatinine measurement data, the outputting section outputs a warning together with the corrected value.

7. The analysis system according to claim 4, wherein the monitoring section monitors further to find abnormality in the fluctuation of the creatinine measurement data, and
   in a case where the monitoring section finds abnormality in the fluctuation of the creatinine measurement data, the outputting section outputs a warning together with the corrected value.

8. An analysis method comprising:
   a creatinine information acquisition step of inputting creatinine measurement data that indicate measured quantity of creatinine in a urine sample;
   a material ingredient information acquisition step of inputting material ingredient data that indicate measured quantity of a bacteria or cast in the urine sample; and
   a correction step of correcting by a computer the measured quantity of the material ingredient indicated as the material ingredient data, by use of the measured quantity of the creatinine indicated as the creatinine measurement data.

9. A non-transitory recording medium on which an analysis program has been recorded, wherein the analysis program allows a computer to execute:
   a creatinine information acquisition process for inputting creatinine measurement data that indicate measured quantity of creatinine in a urine sample;
   a material ingredient information acquisition process for inputting material ingredient data that indicate measured quantity of a bacteria or cast in the urine sample; and
   a correction process for correcting the measured quantity of the material ingredient indicated as the material ingredient data, by use of the measured quantity of the creatinine indicated as the creatinine measurement data.

* * * * *